US009681815B2

(12) United States Patent
Porée et al.

(10) Patent No.: US 9,681,815 B2
(45) Date of Patent: Jun. 20, 2017

(54) RECONSTRUCTION OF A SURFACE ELECTROCARDIOGRAM FROM AN ENDOCARDIAL ELECTROGRAM USING NON-LINEAR FILTERING

(71) Applicant: SORIN CRM S.A.S., Clamart (FR)

(72) Inventors: Fabienne Porée, Rennes (FR); Guy Carrault, Cesson-Sévigné (FR); Amar Kachenoura, Rennes (FR); Alfredo Hernandez, Rennes (FR)

(73) Assignee: SORIN CRM SAS, Clamart (FR)

( * ) Notice: Subject to any disclaimer, the term of this patent is extended or adjusted under 35 U.S.C. 154(b) by 553 days.

(21) Appl. No.: 14/015,770

(22) Filed: Aug. 30, 2013

(65) Prior Publication Data

US 2013/0345580 A1 Dec. 26, 2013

Related U.S. Application Data

(63) Continuation of application No. 12/755,290, filed on Apr. 6, 2010, now Pat. No. 8,527,037.

(30) Foreign Application Priority Data

Apr. 6, 2009 (FR) ..................................... 09 01662

(51) Int. Cl.
*A61B 5/04* (2006.01)
*A61B 5/0402* (2006.01)
(Continued)

(52) U.S. Cl.
CPC .......... *A61B 5/04021* (2013.01); *A61B 5/042* (2013.01); *A61B 5/04028* (2013.01);
(Continued)

(58) Field of Classification Search
CPC ........ A61B 5/7264; A61B 5/72; A61B 5/7235
(Continued)

(56) References Cited

U.S. PATENT DOCUMENTS 5,740,811 A * 4/1998 Hedberg et al. .............. 600/510
6,572,560 B1 6/2003 Watrous et al.
(Continued)

FOREIGN PATENT DOCUMENTS

EP 0 784 996 7/1997

OTHER PUBLICATIONS

Vasquez et al., "Atrial Activity Enhancement by Wiener Filtering Using an Artificial Neural Network", IEEE Transactions on Biomedical Engineering, vol. 48, No. 8, Aug. 2001 pp. 940-944.*
(Continued)

*Primary Examiner* — Amanda Patton
*Assistant Examiner* — Philip C Edwards
(74) *Attorney, Agent, or Firm* — Foley & Lardner LLP (57) ABSTRACT

The present invention relates to an active medical device that uses non-linear filtering for reconstructing a surface electrocardiogram from an endocardial electrogram. At least one endocardial EGM electrogram signal is collected from of samples collected from at least one endocardial or epicardial derivation (71', 72', 73'), and at least one of a reconstructed surface electrocardiogram (ECG) signal through the processing of collected EGM samples by a transfer function (TF) of a neural network (60'). The neural network (60') is a time-delay-type network that simultaneously processes said at least one endocardial EGM electrogram signal, formed by a first sequence of collected samples, and at least one delayed version of this EGM signal, formed by a second sequence of collected samples distinct from the first sequence collected samples. The neural network (60') provides said reconstructed ECG signal from the EGM signal and its delayed version.

20 Claims, 7 Drawing Sheets

(51) Int. Cl.
- *A61B 5/042* (2006.01)
- *A61B 5/00* (2006.01)
- *G06K 9/00* (2006.01)
- *G06K 9/62* (2006.01)
- *H01L 27/146* (2006.01)

(52) U.S. Cl.
CPC ........ *A61B 5/7267* (2013.01); *G06K 9/00503* (2013.01); *G06K 9/6232* (2013.01); *H01L 27/14621* (2013.01); *H01L 27/14627* (2013.01); *H01L 27/14632* (2013.01); *H01L 27/14685* (2013.01); *H01L 27/14687* (2013.01)

(58) Field of Classification Search
USPC .............................. 600/509; 128/697; 607/27
See application file for complete search history.

(56) References Cited

U.S. PATENT DOCUMENTS 6,953,436 B2  10/2005  Watrous et al.
6,980,850 B1  12/2005  Kroll et al.
2008/0013747 A1  1/2008  Tran

OTHER PUBLICATIONS

Elman, "Finding Structure in Time", Cognitive Science, 14, pp. 179-211 (1990).

Elman, JL, "A recurrent Neural Network that Learns to Count," Connection Science, vol. 11, No. 1, 1999, pp. 5-40.

Hornick, Stinchcombe, White, Multilayer Feedforward Networks are Universal Approximator, Neural Networks, vol. 2, pp. 359-366, 1989.

Preliminary Search Report for French Patent Application No. 09-01662, dated Oct. 9, 2009, 2 pages.

Vasquez, A., Hernandez, F., Mora, G., Carrault, G., Passariello: "Atrial Activity Enhancement by Wiener Filtering Using an Artificial Neural Network", IEEE Transactions on Biomedical Engineering, vol. 48, No. 8, Aug. 2001, pp. 940-944.

* cited by examiner

FIG_1 PRIOR ART

FIG_2 PRIOR ART

FIG_3 PRIOR ART

FIG_4

FIG_5

FIG_6

FIG_7

FIG_8

FIG_9

FIG_10

FIG_11

FIG_12

RECONSTRUCTION OF A SURFACE ELECTROCARDIOGRAM FROM AN ENDOCARDIAL ELECTROGRAM USING NON-LINEAR FILTERING

CROSS-REFERENCE TO RELATED APPLICATIONS

This application is a continuation of U.S. patent application Ser. No. 12/755,290, filed on Apr. 6, 2010, which claims the benefit of French Patent Application No. 09-01662, titled "Reconstruction of a Surface Electrocardiogram from an Endocardial Electrogram Using Non-Linear Filtering" filed on Apr. 6, 2009, both of which are hereby incorporated by reference as if set forth herein in their entirety.

FIELD OF THE INVENTION

The present invention relates to "implantable medical devices" such as those defined by the Jun. 20, 1990 Directive 90/385/EEC of the Council of European Communities, specifically to implantable devices that continuously monitor heart rhythm and deliver to the heart, if necessary, electrical stimulation pulses for cardiac resynchronization and/or defibrillation, in case of a rhythm disorder detected by the device. The invention more particularly relates to processing the signals representative of cardiac depolarization potentials of the myocardium, such signals being collected through epicardial or endocardial electrodes for pacing, sensing or defibrillation of the right and left atria or ventricles, of these implantable devices.

Even more particularly, the present invention is directed to a method, whether or not implemented in an implanted device, for the reconstruction of a surface electrocardiogram (ECG) from an endocardial or epicardial electrogram (EGM).

BACKGROUND OF THE INVENTION

It is known that EGM signals can be collected by use of electrodes placed on endocardial or epicardial leads of a device implanted in a patient. These signals, directly related to the electrical activity of cardiac cells of the patient, provide useful information for the purpose of assessing the patient's condition. Hence, after amplifying, conditioning, digitizing and filtering, EGM signals are mainly utilized to control the implanted devices and diagnose rhythm disorders requiring, for example, automatic triggering of an antitachycardia, antibradycardia, or interventricular resynchronization therapy.

However, when it comes to analyzing subjectively the heart rhythm, e.g., to perform a diagnosis or readjust the control/operating parameters of an implanted device, the practitioners prefer, in practice, to interpret the information given by a surface electrocardiogram (ECG). An ECG allows one to visualize in a direct manner, a certain number of determining factors (e.g., QRS width) and thereby assess the evolution of a heart failure.

ECG signals are usually recorded over a long period of time through ambulatory practice by Holter recorders. The recorded ECG signals are then further processed and analyzed in order to evaluate the clinical condition of the patient and eventually diagnose whether a cardiac rhythm disorder is present.

The ECG and EGM signals actually have the same signal source (i.e., the electrical activity of myocardium), however, they visually appear in much different manners: the EGM collected by the implantable device provides local information on the electrical activity of a group of heart cells, whereas the ECG appears in the form of more global information, in particular influenced by the propagation of the electrical signals between the myocardium and body surface, with certain morphologic and pathologic specificities. Thus, the display of EGM signals is not very useful to a practitioner who interprets ECG signals.

When a patient implanted with a medical device comes to his practitioner for a routine visit, two distinct devices are used: an ECG recorder and an external implant programmer. In order to collect the ECG signal, the practitioner places electrodes in particular locations relative to the patient's torso. The ECG signals are collected between predefined pairs of electrodes to define typically twelve "derivations" of the collected ECG signals. The external programmer is used to control certain operating parameters of the implantable device (e.g., the battery life), download data from the implantable device memory, modify the parameters thereof, or upload an updated version of the device operating software, etc.

The visit with the practitioner therefore usually requires these two different devices, as well as specific manipulations for placing the surface electrodes and collecting the ECG signals. Moreover, the use of these two devices requires the patient to come to a specifically equipped center, usually having the consequence that routine visits are spaced farther apart, resulting in a less rigorous follow-up of the patient.

In order to overcome such drawbacks, algorithms have been developed for reconstructing a surface ECG signal based upon collected EGM signals from an implantable device. Some of these algorithms use a neural network. Their functioning is described hereafter in reference to FIGS. 1 and 2, respectively: a first step of learning or developing a transfer function for a neural network and a second step of calculating or reconstructing an ECG signal from a collected EGM signal using a transfer function. EGM signal 1 and ECG signal 3 are collected from the patient and transmitted to neural network 5. Neural network 5 learns and develops a transfer function that delivers ECG signal 3 as an output when the EGM signal 1 is provided as input. When the learning step is done, then for another EGM signal 7 collected from a patient, ECG signal 9 is reconstructed (FIG. 2) as an output signal of this neural network 5 after its transfer function has processed input EGM signal 7.

Figure 3:
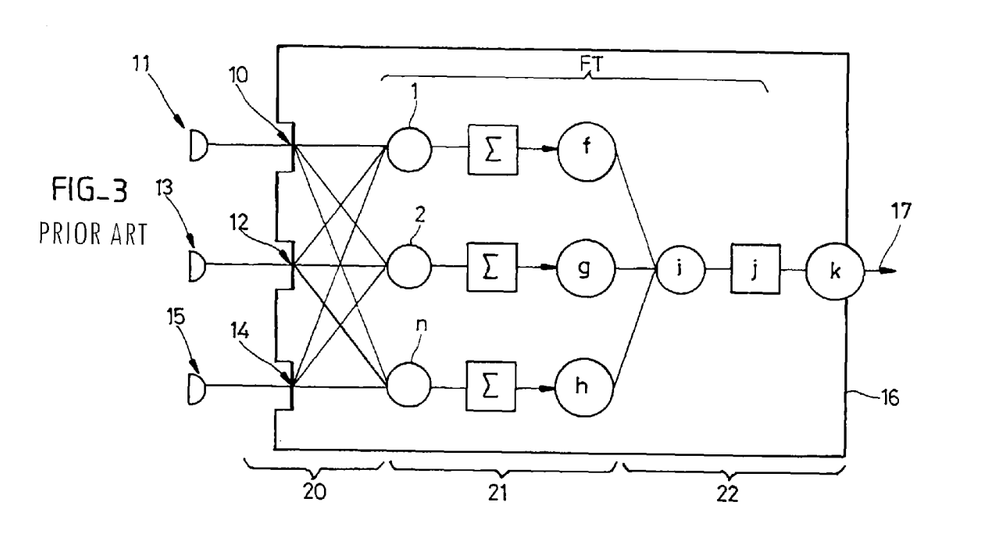
FIG. 3 is a schematic representation of a prior art neural network for reconstructing an ECG according to a feed-forward approach.

The EP patent EP 0 784 996 A1 and its US counterpart U.S. Pat. No. 5,740,811, to Hedberg, et al., propose to synthesize an ECG signal by combining a plurality of EGM signals by means of a neural network and/or fuzzy logic and/or summer circuit, after a learning process performed by an algorithm of a "feedforward" type. Such a prior art network 16 is schematically shown in FIG. 3. Network 16 consists of: a set of inputs 20; a so-called "hidden" layer of neurons or "internal" layer of neurons 21, the inputs and outputs of this layer being not linked with EGM input data or ECG output data, and a layer of output neurons 22. Transfer function FT is calculated in the hidden layer 21 and in the output layer 22. Network 16 receives at its various EGM signals 10, 12 and 14 from different derivations 11, 13 or 15. Network 16 processes these EGM signals 10, 12, and 14 using transfer function FT, with subfunctions f, g, . . . k, and generates a reconstructed ECG signal 17.

Figure 1:
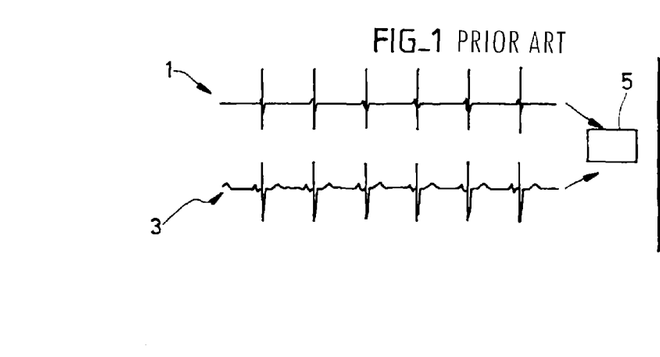
FIGS. 1 and 2 illustrate respectively a prior art learning step and reconstruction step implemented in a prior art neural network.
Figure 2:
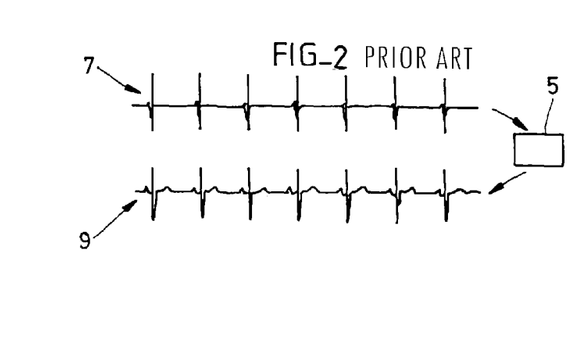

Network 16 learns, as described with reference to FIGS. 1 and 2, transfer function FT by operating a base of learning associated with a template of a specific signal class. Indeed, the learning of neural network 16 is performed between a single ECG beat and a single EGM beat.

Such a solution is not, however, robust. For example, changes in the QT interval during an exercise (e.g., shortening of QT) are unlikely to be taken into account. In addition, if a new morphology beat is collected (e.g., a ventricular extrasystole, junctional beats, or a ventricular originated arrhythmia), network 16 corresponds to an unknown type or template. But neural network 16 cannot translate its learning based on a known type or template to the synthesis of an unknown type or template.

Moreover, network 16 reconstructs ECG signals beat by beat and requires an intermediate step to concatenate the reconstructed beats, which implicates two major problems related to the length of the window of analysis and to the processing of premature events. The reconstruction also requires a preliminary step to detect the QRS wave form, which may lead to detection of defects and, therefore, resulting in false ECG reconstruction.

Finally, neural network 16 requires at least two EGM derivations, i.e., a minimum presence of two collection electrodes as well as a reference electrode (e.g., the device case or CAN), or three collection electrodes.

The use of time-delay networks in the medical field is known and described for example by C. Vasquez et al. *Atrial Activity Enhancement by Wiener Filtering Using an artificial Neural Network*, IEEE Transactions on Biomedical Engineering, Vol. 48, No. 8, August 2001, pp. 940-944, as well as in US 2008/013747 A1 and U.S. Pat. No. 6,572,560 B1. Nevertheless, it is never suggested, and the inventors believe that they are the first to have recognized the possibility to use a time-delay network in generating a reconstructed ECG signal from collected EGM signals directly delivered by an implanted device.

SUMMARY OF THE INVENTION

It is, therefore, an object of the present invention to provide an improved active medical device and process for obtaining a reconstructed surface electrocardiogram through the use of non-linear filtering. One such device comprises: means for collecting at least one endocardial electrogram (EGM) from at least one endocardial or epicardial derivation, using a plurality of endocardial electrodes, and means for computing a reconstructed surface electrocardiogram (ECG) from the collected EGM through the use of a neural network having a learned transfer function.

In a characteristic embodiment of the present invention, the neural network is of a time-delay type that simultaneously processes at least one EGM signal, formed by a first sequence of collected signal samples, and at least one delayed version of the EGM signal, formed by a second sequence of the collected signal samples, wherein the second sequence is distinct from the first sequence, so as to provide the reconstructed ECG signal from the EGM signal and its delayed version.

Such an implanted device has many advantages as a result of processing temporal information provided by use of different sequences of samples from a single EGM signal. In particular, such a device learns a new transfer function to deliver an acceptable reconstructed ECG in the presence of new unlearned beats (for example, ventricular extrasystole, junctional beat or escape, ventricular originated arrhythmia).

Thus, the neural network implements the transfer function that was calculated during the learning step to provide an acceptable result. In other words, a time-delay network is applicable to more general purpose applications than a prior art feed-forward type neural network.

Furthermore, the present invention has an advantage of reconstructing, from a single EGM derivation, signals corresponding to the twelve ECG derivations.

Finally, it should be understood by a person of ordinary skill in the art that such a device can be implemented with neural networks operating in a SISO, MISO or MIMO mode (as defined below).

One aspect of the present invention is directed to an active medical device comprising:
means for collecting at least one endocardial electrogram (EGM) signal, formed of a plurality of signal samples from at least one endocardial or epicardial derivation;
a neural network having a plurality of neurons and a transfer function (FT);
means for reconstructing at least one surface electrocardiogram (ECG) signal through the processing of said collected EGM signal samples by said transfer function (FT), wherein the neural network is a time-delay type network simultaneously processing said at least one EGM signal having a first sequence of said plurality of collected signal samples, and at least one delayed version of said at least one EGM signal having a second sequence of said plurality of collected signal samples, said second sequence being distinct from said first sequence. Optionally, the first sequence and the second sequence have the same number of temporally shifted samples.

In one preferred embodiment, the device further comprises means for determining the transfer function (TF) of the neural network using simultaneous collections of said at least one EGM signal and at least one ECG signal. According to another embodiment, the device further comprises means for simultaneously collecting said at least one EGM signal and said at least one ECG signal over a series of successive cardiac cycles.

In yet another embodiment, the device comprises means for determining the transfer function of the neural network from at least two collected EGM signals using at least two EGM derivations. The neural network comprises:
at least two inputs receiving the at least two collected EGM signals on at least two derivations, and a transfer function (TF) that processes said EGM signals and their delayed versions and provides at least one reconstructed ECG signal from said EGM signals and their said delayed versions. Optionally, the device comprises means for determining the transfer function (TF) from at least two collected ECG signals on at least two ECG derivations. The neural network comprises at least two inputs receiving the at least two collected EGM signals on different derivations, wherein the transfer function processes said collected EGM signals and their delayed versions and provides at least two reconstructed ECG signals from said at least two collected EGM signals and their delayed versions.

Another embodiment of a device in accordance with the present invention comprises means for determining the transfer function (TF) by receiving as input a group of n EGM signals, from the same derivation, said group including an EGM signal and n−1 differently delayed versions of said EGM signal, where n is selected from between 2 and 50.

In yet another preferred embodiment, the means for collecting the at least one EGM signal further comprises means for collecting samples of an EGM signal by performing sequences of measurements with a frequency selected from between 1 Hz and 100 kHz. Optionally, the collecting means further comprises means for recording an EGM sequence of from 1 to 200 beats.

Another preferred embodiment of the device in accordance with the present invention comprises means for shifting the first sequence of samples vis-à-vis the second sequence of samples by a step of about 0.01 s.

According to one embodiment, the reconstructed ECG signal is calculated over several different beats.

In a preferred embodiment, the neural network is a time delayed structure selected from a group of a Focused Time-Delayed Neural Network (FTDNN) and a Distributed Time-Delayed Neural Network (DTDNN). Alternately, the neural network may be a recurrent structure.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed, in which like reference characters refer to like elements, and in which.

DETAILED DESCRIPTION OF THE INVENTION

With reference to the drawings, embodiments of the device of the present invention will now be described. Preferably, the functionality and processes of the present invention as described herein can be implemented by an appropriate software programming of a known implantable pulse generator, for example, a pacemaker or defibrillator/cardioverter, comprising known and conventional circuits and signal acquisition and processing algorithms for acquiring a signal provided through endocardial leads and/or several implanted sensors.

As used herein, it should be understood that the terms "ECG" or "EGM" may be used interchangeably with the terms "ECG signal" or "EGM signal."

The present invention uses a specific approach for each patient based on a time-delay type neural network. The time-delay type neural network reconstructs an ECG signal from an endocardial electrogram (EGM) collected from an endocardial and/or epicardial derivation, said signals being collected through an endocardial or epicardial electrode.

Figure 4:
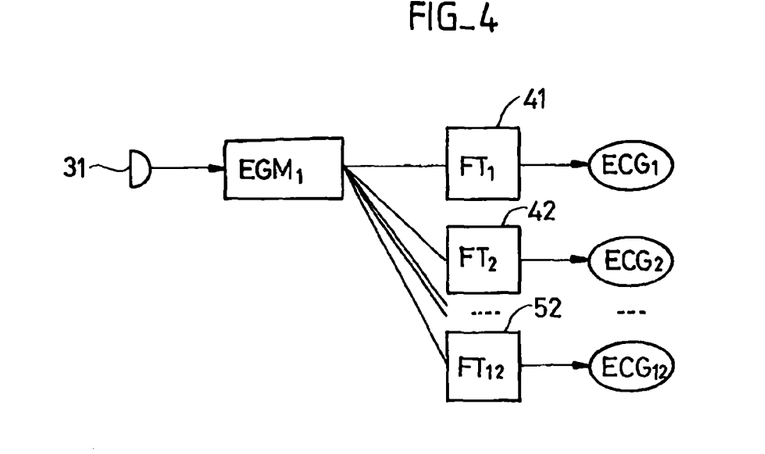
FIGS. 4, 5 and 6 are schematic representations of neural networks in accordance with the present invention.
Figure 5:
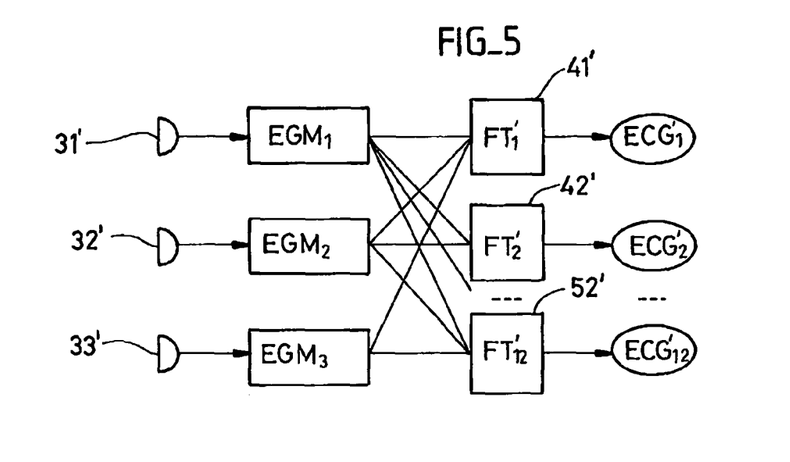
Figure 6:
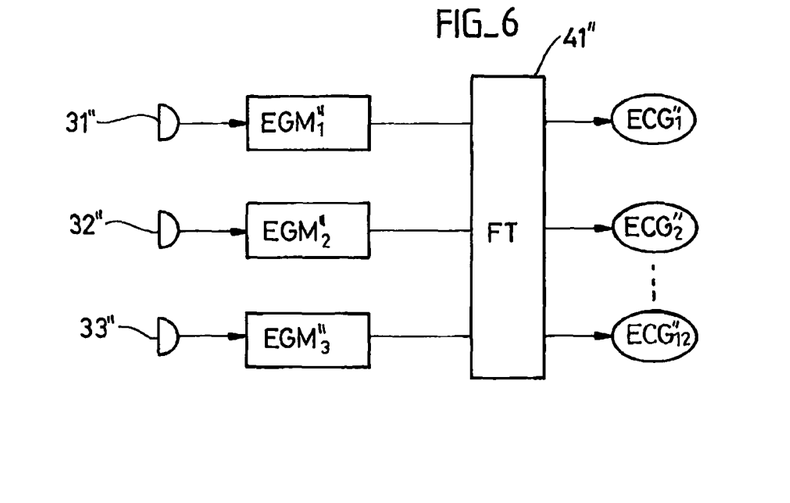

Referring to FIGS. 4, 5 and 6, three alternative embodiments of neural networks in accordance with the present invention are schematically represented. FIG. 4 illustrates a first embodiment wherein a single derivation 31 delivers an EGM1 signal to networks 41, 42, . . . 52. Each of these networks 41, 42, . . . 52 uses its transfer function FT1, FT2, . . . FT12 to deliver as output reconstructed signals ECG1, ECG2 . . . , ECG12, each output corresponding to one of twelve external ECG derivations. In this embodiment, network 41, 42 . . . 52 run in a SISO ("Single Input Single Output") system.

FIG. 5 illustrates a second embodiment wherein a plurality of EGM1', EGM2' and EGM3' signals collected from distinct derivations 31', 32' and 33' is processed by each network 41', 42' . . . 52', using its transfer function FT1' FT2' . . . FT12' to provide as outputs reconstructed signals ECG1', ECG2' . . . and ECG12', each corresponding to one of twelve external ECG derivations. In this embodiment, each of these networks 41', 42' . . . 52' operates on a MISO ("Multiple Input Single Output") system.

FIG. 6 illustrates a third embodiment, a plurality of EGM1", EGM2" and EGM3" signals collected from distinct derivations 31", 32" and 33" is processed by a network 41" using its transfer function FT to provide as output reconstructed signals ECG1", ECG2" . . . ECG12", each corresponding to one of twelve external ECG derivations. In this embodiment, the network 41" operates in a MIMO ("Multiple Input Multiple Output") system.

Figure 7:
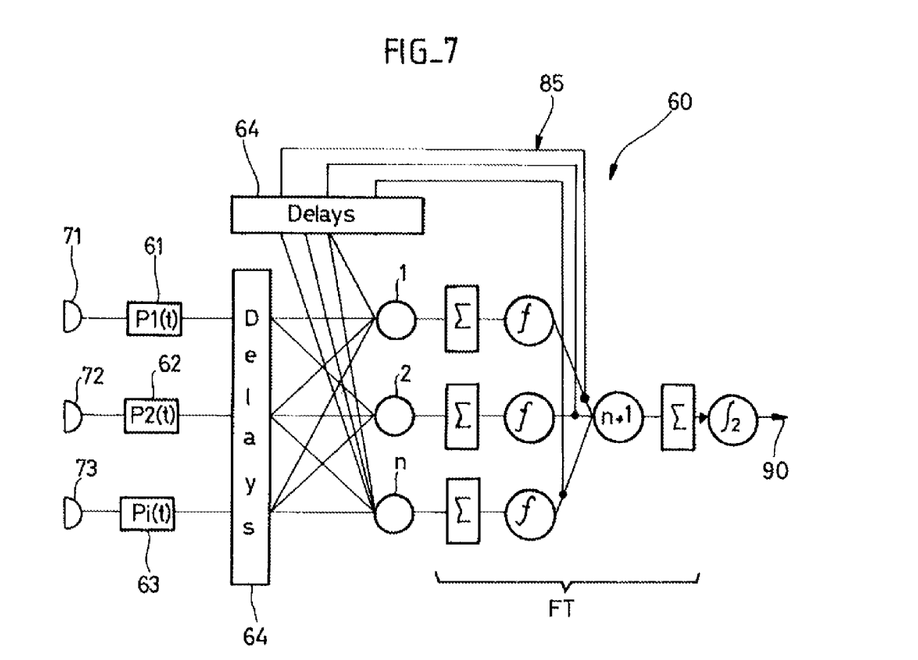
FIGS. 7 and 8 are functional diagrams of neural networks in accordance with embodiments of the present invention.
Figure 8:
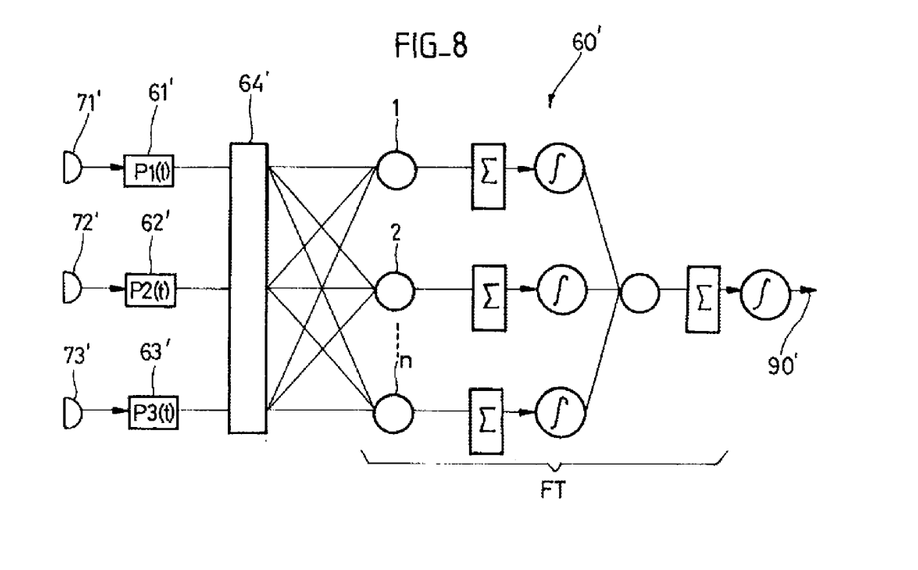
Figure 9:
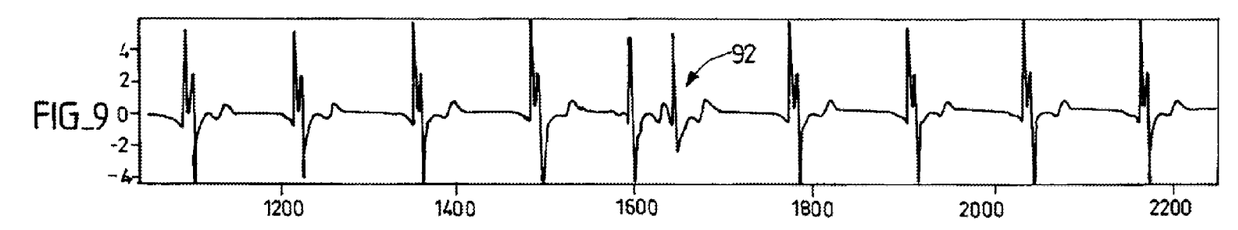
FIGS. 9, 10, 11 and 12 are respectively representations of an EGM signal, an ECG signal simultaneously collected, an ECG signal reconstructed according to the prior art, and an ECG signal reconstructed according to the invention.
Figure 10:
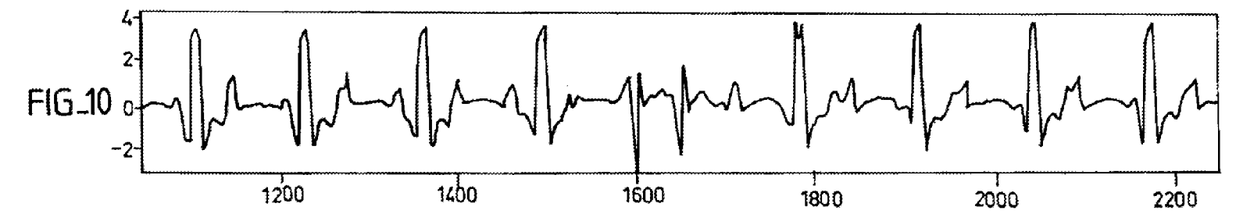

According to one embodiment of the present invention, each of these embodiments of networks 41, 42 . . . , 52 (FIG. 5); 41', 42' . . . , 52' (FIG. 6), and 41, 42" . . . 52" (FIG. 7), is of a time-delay type, for example, as described with reference to FIGS. 7 and 8. Time-delay network 60 of a recurrent type as shown in FIG. 7 comprises:

inputs 61, 62 and 63 receiving EGM signals collected on different derivations 71, 72 and 73;

recurrent connections 85, receiving signals processed by the hidden layer of the network 60;

buffers 64 introducing a time delay on the input EGM signals and on data on the recurrent connections 85; and a transfer function FT for processing the collected EGM signals on derivations 71, 72 and 73, and the delayed versions of these signals 85 and providing reconstructed ECG signal 90.

It should be understood that each processed signal—and its delayed version—consists of a sequence of samples—that is to say—measurements extracted from the sampled signals forming a collected EGM signal. Preferably, the neural networks according to the present invention simultaneously process at least one EGM signal formed by a first sequence of collected signal samples and at least one delayed version of the EGM signal, formed by a separate second sequence of said collected signal samples separate of the samples of the first sequence.

In a first embodiment, the EGM signal and its delayed version are two sequences in which samples are shifted by one step p of about 0.01 s, or more generally a step p selected from between 0.001 and 0.1 s. Thus, assuming a signal sample comprising two hundred samples (1, 2, 3, 4, 5, . . . 100, 101, 102, . . . 200), the first sequence may comprise the samples (1, 2, 3, 4, 5, 6, 7, 8, 9, . . . 100) while the second sequence includes the samples (d+1, d+2, . . . d+1 00) with d=p*fe, where fe is a sampling frequency and p is the step between sequences. For example if p=0.01 s, and fe=100 Hz then d=1. Another example, if p=0.01 s and fe=1 kHz then d=10. A third example is if p=0.02 s and if fe=1 kHz, then d=20.

According to one embodiment of the present invention, for a given collected signal, a plurality of delayed versions with different shifts is used between samples of a same sequence and/or between samples of different sequences.

Another embodiment of the present invention is described with reference to FIG. 8. Time-delay network 60' has no recurrence and comprises:

inputs 61', 62' and 63' receiving EGM signals collected on derivations 71', 72' and 73;

buffers 64' introducing a time delay on the input EGM signals; and a transfer function FT for processing the EGM signals and their delayed versions and providing reconstructed ECG signal 90'.

It is appreciated that different structures of time-delay networks can be implemented, with or without a recurrent approach without deviating from the scope of the present invention. For example, a neural network according to the present invention is selected from a group of:

a FTDNN ("Focused Time-Delayed Neural Networks"), and a DTDNN ("Distributed Time-Delayed Neural Networks").

For example, too, such recurrent approaches may be selected from a group of:

Elman,

Hopfield net structure; and

ARX (AutoRegressive neural network with eXogenous input).

According to another embodiment of the present invention, Recurrent Time-Delayed Neural Networks (RTDNN) is used by combining both a time-delay approach and a recurrent approach. Time delay approaches are described in K. Mr. Hornik and Stinchcombe, "Multilayer feedforward networks are universal approximator," Neural Networks, Vol. 2, No. 5 pp. 359-366, 1989. The TDNN approach is described in Elman, J L, "Finding structure in time," Cognitive Science, Vol. 14, pp. 179-211, 1990, for the ELMAN approach. The RTDNN approach is described on Rodriguez, P., Wiles, J., and Elman, J. L. "A recurrent neural network that learns to count," Connection Science, Vol 11, No. 1, pp. 5-40, 1999.

Once the structure of the time-delay neural network is selected, the following two steps are performed:

A first step, known as learning, in which the time-delay neural network learns and determines an optimal transfer function between at least one EGM signal and at least one ECG signal that is simultaneously collected as inputs, and generates at least one reconstructed ECG signal as an output. This learning process may be done during or subsequent to implantation of the device so that EGM and ECG signals are simultaneously collected. During this first step, the inputs used to determine the transfer function are at least one EGM signal and at least one ECG signal simultaneously collected.

In addition, learning over several successive beats (cardiac cycles) may allow the reconstruction of an ECG signal with multiple morphologies when these multiple morphologies are present during the learning phase. Preferably, the learning is done by recording (collecting) EGM and ECG over successive beats.

The time-delay network performs learning on synchronous EGM and ECG signals to ensure subsequent reconstruction of an ECG signal with a particularly high level of similarity.

According to one embodiment, the collection of the signals comprises one or more of the following steps:

an optional step of low pass filtering of at least one ECG signal and of at least one EGM signal at 45 Hz, an optional step of sub-sampling of ECG and EGM signals, to reduce computational costs, a step of network optimization (e.g., number of delays, parameters values for the convergence test).

In a preferred embodiment, the device comprises an input layer with 15 inputs represented by three EGM derivations (ProxA, proxVD, distVD) at time t and 4 delayed versions with a step of p=0.01 s (i.e., a single sample delay for fe=100 Hz, and thus a maximum global shift of 4 samples) for each EGM derivation. The hidden layer of the neural network consists of 50 neurons forming the transfer function FT.

During a second step for reconstructing the ECG signal, the neural network performs the synthesis of the collected ECG(s) from the collected EGM(s) using the learned (or determined) transfer function FT. The same EGM derivations are used for the reconstruction phase as during the learning phase.

In a preferred application, the EGM(s) are collected by the implanted device and the ECG(s) are reconstructed by applying the transfer function that has been determined during the learning step.

Specifically, the output signal of the network is one or more reconstructed ECG(s) using the same derivation as in the learning phase and based on one or more of the following steps:

an optional step of 45 Hz low-pass filtering of the EGM signal(s);

an optional step of sub-sampling of EGM data when this sub-sampling was conducted before the network optimization phase;

an application of the network to the EGM data.

From such signals, a time-delay type neural network reconstructs the twelve derivations of an ECG. In one embodiment, the neural network of this type comprises 5 neurons to get that result.

As previously described, the time-delay type of neural network, as the one described in the present invention, is able to learn a new transfer function between an input and an output signals. It is thus able to generate a reconstructed ECG signal even in the presence of new unlearned beats (e.g., ventricular extrasystole, junctional escape, ventricular originated arrhythmia). The network applies the transfer function that was calculated during the learning phase and it provides a likely result. This type of network, therefore, provides larger generalization capabilities than other neural networks.

Referring to FIGS. 9, 10, 11 and 12, EGM signals (FIG. 9) or simultaneously collected ECG signals (FIG. 10), a reconstructed ECG signal of the prior art (FIG. 11) and a reconstructed ECG signal according to the present invention (FIG. 12) are respectively represented. In the presence of unlearned beats 92, reconstructed ECG signal (FIG. 11) according to the prior art fails to while the reconstructed ECG signal (FIG. 12) according to the invention generates an irregular beat 94.

Figure 11:
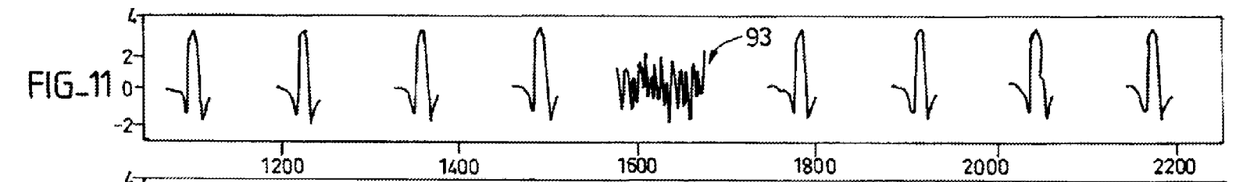
Figure 12:
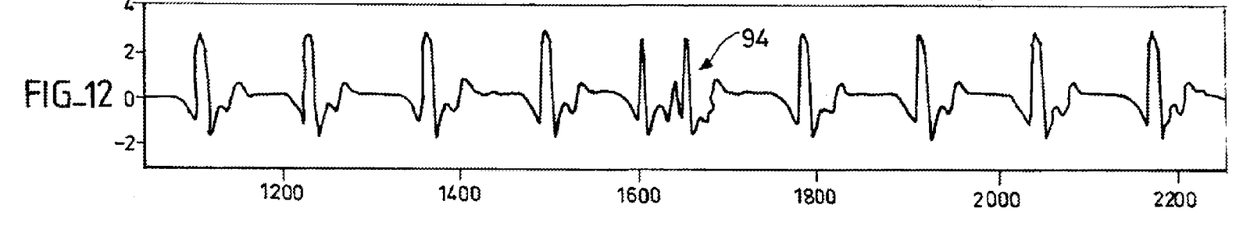

In general, the comparison of the wave forms of a prior art reconstructed ECG signal and a reconstructed ECG signal reconstructed according to one of the embodiments of the present invention, respectively illustrated in FIGS. 11 and 12, emphasizes several advantages of using a time-delay network having performed the learning on synchronous EGM and ECG signals, namely:

a reconstruction that is particularly likely and allows to reconstruct a continuous signal (e.g., P, QRS, T and the baseline). This eliminates the need for performing a detection step of the QRS complex;

avoidance of the problems related to windowing (choice of the width of the timing window and concatenation of the reconstructed intervals);

a better resistance to changes in rhythm is achieved.

Figure 13:
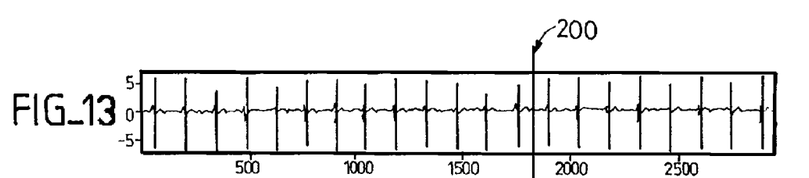
FIGS. 13, 14 and 15 are respectively representations of an EGM signal and an ECG signal simultaneously collected, and a reconstructed ECG signal according to the present invention during a sinus rhythm.
Figure 14:
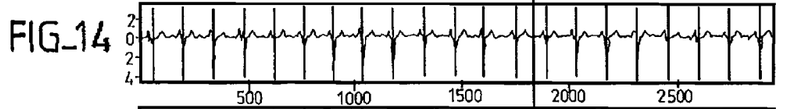
Figure 15:
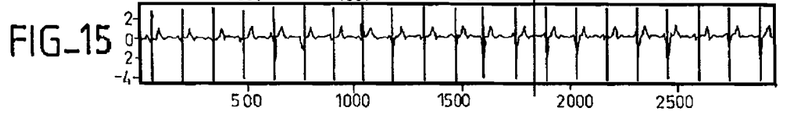

The quality of reconstruction is also noticeable, while reproducing sinus beats by comparing the measured ECG signal (FIG. 14) and the measured EGM signal (FIG. 13) to the reconstructed ECG signal according to the present invention (FIG. 15).

Figures 16, 17, 18:
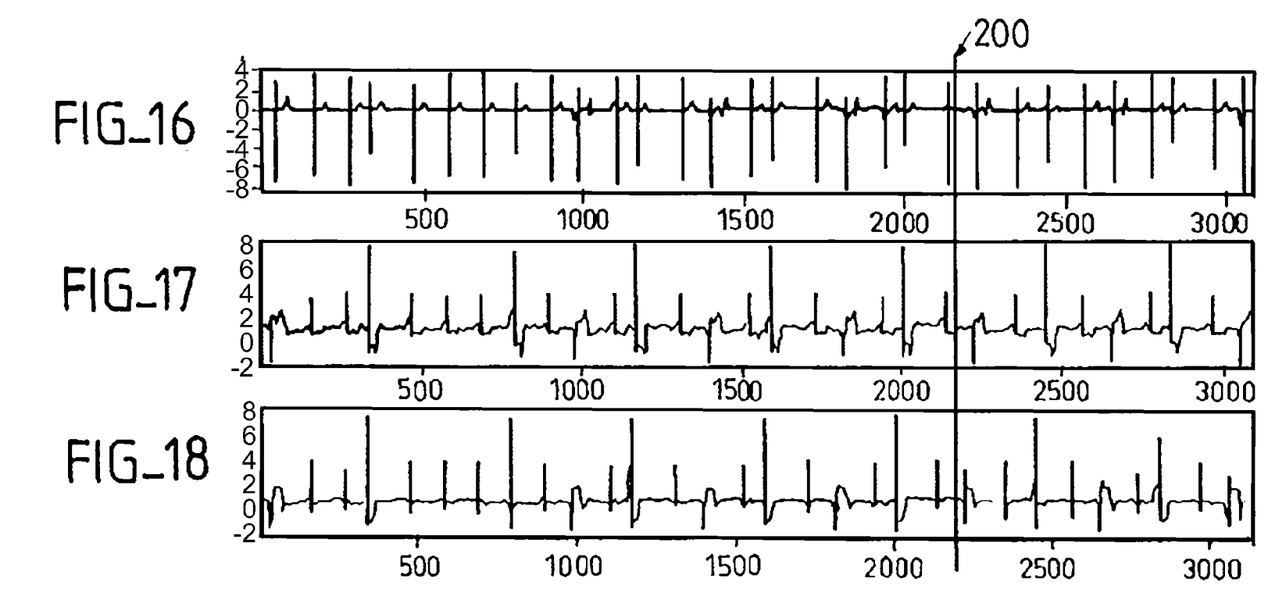
FIGS. 16, 17 and 18 are respectively representations of an EGM signal and an ECG signal simultaneously collected, and a reconstructed ECG signal according to the present invention and presenting multiple beat morphologies.

In addition, because the network learning phase is conducted over several successive beats that may be of different morphologies, ECG signals may be reconstructed with multiple morphologies. In other words, in the case of a patient whose ECG beats contain multiple morphologies, all morphologies are reconstructed through a learning process over several successive beats as shown in FIGS. 16, 17 and 18. In this case the device performs learning on synchronous EGMs and ECGs and therefore can provide a particularly likely reconstruction.

Figure 19:
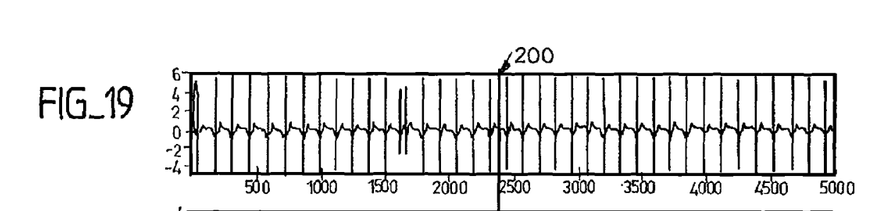
FIGS. 19, 20 and 21 are respectively representations of an EGM signal and an ECG signal simultaneously collected, and a reconstructed ECG signal according to the present invention presenting a ventricular doublet.
Figure 20:
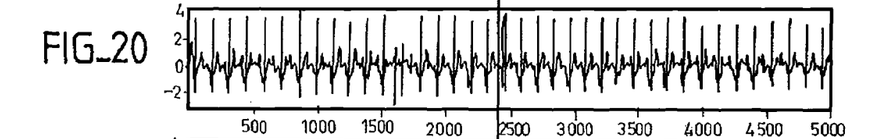
Figure 21:
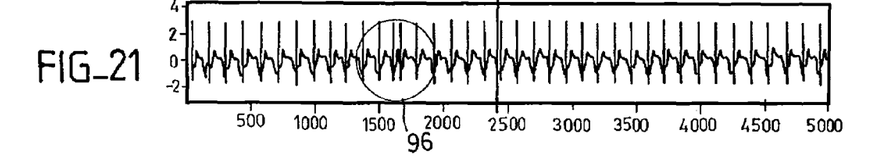

Finally, in the presence of an unlearned arrhythmia (EGM of FIG. 19, associated with the measured ECG signal in FIG. 20), the reconstructed beat according to the invention (FIG. 21, rep. 96) is obviously different from the other beats, allowing the detection of the unlearned arrhythmia.

It should be understood that performing a learning phase on synchronous EGM and ECG ensures that the corresponding beats are correctly presented as inputs and targets to the neural network. A separation 200 between the learning phase and the phase of detection is shown in FIGS. 13 to 21.

It should be understood that numerous variants are possible with the present invention without deviating from its scope. Notably, EGM signals may be collected through a plurality of endocardial electrodes or, alternatively, according to such a unipolar mode that the EGM signals are collected through an endocardial electrode and a housing CAN or any other element to measure a potential change at the endocardial electrodes.

Furthermore, it is clear that the sampling frequency of a signal can vary depending on applications.

Numerous other variants can be made in accordance with the present invention. For example, the reconstruction of ECG signal(s) may be done with a time delay neural network, in accordance with the invention, within an implanted device or in a deported device located outside of the human body, said deported device receiving data recorded by a device implanted in the human body.

Preferably, the functionality and processes of the present invention as described herein can be implemented by an appropriate programming of software of a known implantable pulse generator, for example, a pacemaker or defibrillator/cardioverter, comprising known and conventional circuits and signal acquisition and processing algorithms for acquiring a signal provided through endocardial leads and/or several implanted sensors.

The invention can advantageously be applied to and implemented in the commercial implantable devices marketed by Sorin CRM, Montrouge France, such as the Reply™ and Paradym™ brand pacemakers and comparable commercial and/or proprietary devices of other manufacturers. These devices are equipped with programmable microprocessors, including circuits intended to acquire, condition and process electrical signals collected by implanted electrodes and various sensors, and deliver pacing pulses to implanted electrodes. It is also possible to upload towards these devices, by telemetry, pieces of software (i.e., a software control module) that will be stored in internal memory and run so as to implement the features and functionality of the present invention, as described herein. Implementing the features of the invention into these devices is believed to be easily within the abilities of a person of ordinary skill in the art, and will therefore not be described in detail.

One skilled in the art will appreciate that the present invention can be practiced by embodiments other than those described herein, which are provided for purposes of illustration and not of imitation.

The invention claimed is:

1. A method for reconstructing electrocardiogram signals, the method comprising:
   obtaining at least one endocardial electrogram (EGM) signal, formed from a plurality of signal samples from at least one endocardial or epicardial derivation;
   obtaining a transfer function; and
   generating, with a time-delay type neural network, a first surface electrocardiogram (ECG) signal from the at least one EGM signal by simultaneously processing (A) the at least one EGM signal and (B) at least one delayed version of the of the at least one EGM signal, wherein the time-delay neural network is selected from a group comprising a focused time-delay neural network, a distributed time-delay neural network, and a recurrent time-delay neural network.

2. The method of claim 1, further comprising adapting the transfer function responsive to the at least one EGM signal.

3. The method of claim 1, wherein obtaining at least one EGM signal further comprises transferring the at least one EGM signal from an implantable cardiac device.

4. The method of claim 1, wherein obtaining the transfer function further comprises training the transfer function responsive to a first training signal comprising at least two continuous heartbeats.

5. The method of claim 1, wherein obtaining the transfer function further comprises training the transfer function responsive the at least one EGM signal and at least one simultaneously collected ECG signal.

6. The method of claim 1, wherein obtaining the transfer function further comprises training the transfer function responsive to an EGM signal and a plurality of differently delayed versions of the EGM signal.

7. The method of claim 1, further comprising generating, with a second time-delay type neural network and second transfer function, a second surface ECG signal from the at least one EGM signal by simultaneously processing (A) the at least one EGM signal and (B) at least one delayed version of the of the at least one EGM signal.

8. A system for reconstructing electrocardiogram signals, the system comprising:
   an implantable device configured to acquire at least one endocardial electrogram (EGM) signal, formed from a plurality of signal samples from at least one endocardial or epicardial derivation; and
   a time-delay neural network having a plurality of neurons and a transfer function, wherein the time-delay neural network generates a surface electrocardiogram (ECG) signal by simultaneously processing (A) the at least one EGM signal and (B) at least one delayed version of the at least one EGM signal, the time-delay neural network is selected from a group comprising a focused time-delay neural network, a distributed time-delay neural network, and a recurrent time-delay neural network.

9. The system of claim 8, wherein the time-delay neural network is external to the implantable device.

10. The system of claim 8, wherein the implantable device is configured to store the at least one EGM signal for a predetermined amount of time.

11. The system of claim 8, wherein the transfer function is trained responsive to a first training signal comprising at least two continuous heartbeats.

12. The system of claim 8, wherein the transfer function is trained responsive the at least one EGM signal and at least one simultaneously collected ECG signal.

13. The system of claim 8, wherein the transfer function is trained responsive to an EGM signal and a plurality of differently delayed versions of the EGM signal.

14. The system of claim 8, further comprising a second time-delay type neural network and second transfer function configured to generate a second surface ECG signal by simultaneously processing (A) the at least one EGM signal and (B) at least one delayed version of the of the at least one EGM signal.

15. A system for reconstructing electrocardiogram signals, the system comprising:
at least one processor;
a computer readable storage device storing instructions therein, the instructions, when executed by the at least one processor, cause the at least one processor to:
obtain at least one endocardial electrogram (EGM) signal, formed from a plurality of signal samples from at least one endocardial or epicardial derivation;
obtain a transfer function; and
generate, with a time-delay type neural network, a first surface electrocardiogram (ECG) signal from the at least one EGM signal by simultaneously processing (A) the at least one EGM signal and (B) at least one delayed version of the of the at least one EGM signal, wherein the time-delay neural network is selected from a group comprising a focused time-delay neural network, a distributed time-delay neural network, and a recurrent time-delay neural network.

16. The system of claim 15, wherein execution of the instructions further cause the at least one processor to adapt the transfer function responsive to the at least one EGM signal.

17. The system of claim 15, wherein execution of the instructions further cause the at least one processor to train the transfer function responsive to a first training signal comprising at least two continuous heartbeats.

18. The system of claim 15, wherein execution of the instructions further cause the at least one processor to train the transfer function responsive the at least one EGM signal and at least one simultaneously collected ECG signal.

19. The system of claim 15, wherein execution of the instructions further cause the at least one processor to train the transfer function responsive to an EGM signal and a plurality of differently delayed versions of the EGM signal.

20. The system of claim 15, wherein execution of the instructions further cause the at least one processor to generate, with a second time-delay type neural network and second transfer function, a second surface ECG signal by simultaneously processing (A) the at least one EGM signal and (B) at least one delayed version of the of the at least one EGM signal.

* * * * *